United States Patent [19]

Skorianetz et al.

[11] 4,341,666
[45] Jul. 27, 1982

[54] PERFUMING WITH OXYGEN CONTAINING DERIVATIVES OF TRICYCLO[6.2.1.0$^{2,7}$]UNDECANE

[75] Inventors: Werner Skorianetz, Dardagny; Günther Ohloff, Bernex, both of Switzerland

[73] Assignee: Firmenich SA, Geneva, Switzerland

[21] Appl. No.: 249,118

[22] Filed: Mar. 30, 1981

Related U.S. Application Data

[62] Division of Ser. No. 54,028, Jul. 2, 1979, Pat. No. 4,311,852.

[30] Foreign Application Priority Data

Jul. 5, 1978 [CH] Switzerland .......................... 7320/78

[51] Int. Cl.$^3$ ................................................ A61K 7/46
[52] U.S. Cl. ............................... 252/522 R; 252/89.1;
                                                   252/DIG. 13; 252/132
[58] Field of Search ....................... 252/522, 89.1, 132

[56] References Cited

U.S. PATENT DOCUMENTS

| | | | |
|---|---|---|---|
| 3,953,534 | 4/1976 | Sundt | 252/522 X |
| 3,968,070 | 7/1976 | Sundt | 252/522 X |
| 3,979,338 | 9/1976 | Sundt | 252/522 |
| 4,003,935 | 1/1977 | Sundt | 252/522 X |
| 4,118,343 | 10/1978 | Skorianetz et al. | 252/522 |
| 4,273,714 | 6/1981 | Becker | 252/522 X |
| 4,289,660 | 9/1981 | Schaper | 252/522 |

*Primary Examiner*—Joseph M. Golian
*Attorney, Agent, or Firm*—Pennie & Edmonds

[57] ABSTRACT

New oxygen containing derivatives of tricyclo[6.2.1.0$^{2,7}$]undecane useful as perfuming or flavor-modifying ingredients in the manufacture of perfumes, perfumed articles, artificial flavors, foodstuffs, feedstuffs, beverages, pharmaceutical preparations or tobacco products.

Perfume or flavoring compositions containing same as organoleptically active ingredients.

2 Claims, No Drawings

PERFUMING WITH OXYGEN CONTAINING DERIVATIVES OF TRICYCLO[6.2.1.0$^{2,7}$]UNDECANE

This is a division of application Ser. No. 054,028, filed July 2, 1979, now U.S. Pat. No. 4,311,852.

THE INVENTION

The invention refers to novel tricyclic compounds useful as perfuming or flavor-modifying ingredients, more precisely to compounds having the formula

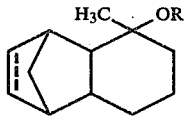
(I)

possessing a single or double bond in the position indicated by the dotted line and wherein symbol R represents either a hydrogen atom, or a saturated or unsaturated acyl radical containing from 1 to 6 carbon atoms.

The invention also refers to a method for modifying, improving or enhancing the organoleptic properties of perfumes, perfumed articles, artificial flavors, foodstuffs, feedstuffs, beverages, pharmaceutical preparations or tobacco products, which comprises adding thereto an effective amount of a compound of formula (I) as set forth hereinabove.

The invention also refers to a perfume or flavour composition containing a compound of formula (I), as set forth hereinabove, as organoleptically active ingredient.

BACKGROUND OF THE INVENTION

Until now, natural products of vegetal or animal origin such as concretes, absolutes, balsams or essential oils, for example, have been widely used in the art of perfumery for the manufacture of perfumes. Due to the extensive use of perfumed products, cosmetics for example, in our modern society or to the perfuming of new materials, the consumption of such natural products is constantly increasing. The industry is therefore often confronted with the problems of scarcity or even disappearance of some of these natural products, essential oils in particular. In this respect, one can cite essential oils such as clary sage oil (*Salvia sclarea*) or sweet marjoram oil (*Origanum Majorana*), both highly appreciated and extensively used in modern perfumery, especially for "masculine" lines. The production of these rather expensive essential oils eminently depends on the climatic conditions, which often vary from season to season. Thus, the amounts produced may be sometimes drastically reduced and that quality of the oil can vary from one harvest to the other.

It is therefore necessary for the perfume or flavor industry to have available synthetically prepared chemical compounds which are able to reproduce, at least partially, some of the organoleptic effects of essential oils such as those mentioned hereinabove. Such chemical compounds would have the advantages of being prepared in practically unlimited amounts and presenting a constant olfactive or gustative effect.

The object of the present invention is aimed at providing the man in the art with a new class of odoriferous chemical compounds possessing useful organoleptic properties, thereby enabling the man in the art to satisfactorily reproduce, in certain instances, some of the olfactive effects typical of clary sage oil or sweet marjoram oil.

This result was quite surprising in view of the prior art which did not suggest that such tricyclic chemical compounds would develop the olfactive characters discussed hereinabove. On the contrary, the prior art teaches that the compound of formula

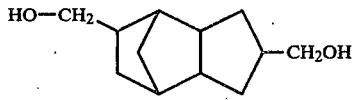

possesses a musky odor—see DE-OS No. 23 07 627—whereas compounds of formulae

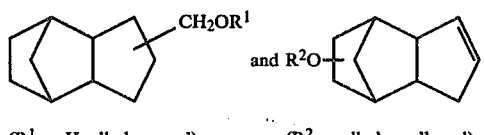

($R^1$ = H, alkyl or acyl)   ($R^2$ = alkyl or alkenyl)

are characterized by their typically flowery, fruity and woody odor in the former case, and by their fruity, green and balsamic odor notes in the latter case—see DE-OS Nos. 26 54 268 and 26 42 519, respectively.

The compound of formula

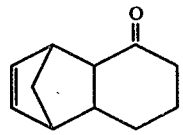

finally, is known in the art for its typically aromatic and "medicinal" odor note, reminiscent of that of wormwood (*Artemisia absinthium*) or liatris—see DE-OS No. 27 37 525.

PREFERRED EMBODIMENTS OF THE INVENTION

In formula (I) as previously defined, symbol R may represent a hydrogen atom or an acyl radical such as formyl, acetyl, propionyl, butyryl, isobutyryl or acrylyl for example. Of particular interest are the following compounds: 3-methyl-tricyclo[6.2.1.0$^{2,7}$]undec-9-en-3-yl acetate, 3-methyl-tricyclo[6.2.1.0$^{2,7}$]undec-3-yl acetate and 3-methyl-tricyclo[6.2.1.0$^{2,7}$]undec-9-en-3-yl formate. More particularly, 3-methyl-tricyclo[6.2.1.0$^{2,7}$]undec-9-en-3-yl acetate having the formula

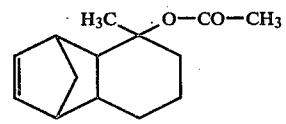

develops an original odor, at the same time fresh, green and natural, reminiscent of some of the olfactive effects of clary sage oil. The above compound is particularly useful as an ingredient for preparing numerous perfume compositions, especially compositions of green, fresh, woody or chypre type, for example. It was observed, in particular, that the addition of the above compound to "masculine" perfume compositions conferred thereto an original and lifting character.

The corresponding saturated derivative, viz. 3-methyl-tricyclo[6.2.1.0²,⁷]undec-3-yl acetate presents the same features, whereas 3-methyl-tricyclo[6.2.1.0²,⁷]undec-9-en-3-yl formate develops, moreover, a typical woody, amber-like and aromatic odor note, reminiscent of that of sweet marjoram oil.

Compounds of formula (I) can be widely used, both in fine and technical perfumery, for instance, for perfuming articles such as soaps, detergents, cosmetics or household materials. For the preparation of perfume compositions, the most interesting odoriferous effects can be achieved by using proportions on the order of between about 0.5 and 20% of the weight of the said composition. Proportions higher or lower that those given hereinabove may also be used, for example, when special effects are desired or for the preparation of perfume bases.

In the field of flavors, compounds of formula (I) are characterized by their green, woody and earthy flavor note, reminiscent of that of pine or vetiver oil, or of bornyl acetate. They can advantageously be used for preparing various artificial flavors or for the aromatization of foodstuffs, beverages, pharmaceutical preparations or tobacco products. For the preparation of flavoring compositions, the above compounds can be used in proportions on the order of about 0.5 to 5% of the weight of the said composition.

Compounds of formula (I) can be easily prepared from tricyclo[6.2.1.0²,⁷]undec-9-en-3-one, after reaction thereof with methyl-magnesium chloride, bromide or iodide e.g., under the conditions of a Grignard reaction. The tertiary alcohol of formula

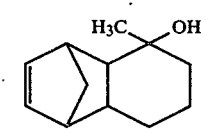
(Ia)

resulting from the above reaction is then converted into the corresponding ester according to the usual techniques, for example, by treating it with a compound of formula

R—Y    (II)

wherein Y represents a halogen atom, chlorine or bromine e.g., or an O-acetyl radical and R a saturated or unsaturated acyl radical containing from 1 to 6 carbon atoms. 3-Methyl-tricyclo[6.2.1.0²,⁷]undec-9-en-3-yl formate e.g. is prepared from the above alcohol (Ia), after treatment thereof with mixed formic-acetic anhydride [Y=O-acetyl; R=formyl in formula (II)]. Similarly the above alcohol can be converted into 3-methyl-tricyclo[6.2.1.0²,⁷]undec-9-en-3-yl acetate by treating it with acetyl chloride [Y=Cl; R=acetyl in formula (II)].

The corresponding saturated esters can be prepared by directly hydrogenating the above cited compounds or by first hydrogenating alcohol (Ia) in the presence of a metal catalyst such as palladium on charcoal, Raney nickel or platinum oxide e.g. to yield the compound of formula

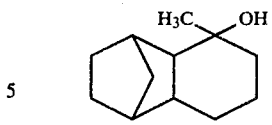
(Ib)

with subsequent esterification thereof effected as described hereinabove.

Tricyclo[6.2.1.0²,⁷]undec-9-en-3-one, used as a starting material, is a known compound which can be obtained from cyclohex-2-en-1-one and cyclopentadiene according to known methods (see: J. Org. Chem. 39, 3063 (1974) and DE-OS No. 27 37 525).

The following examples, wherein the temperatures are given in degrees centigrade and the abbreviations have the usual meanings, are set forth to illustrate the invention in a more detailed way.

EXAMPLE 1

3-Methyl-tricyclo[6.2.1.0²,⁷]undec-9-en-3-ol

To a suspension of 4.55 g (0.187 mole) of magnesium turnings in 10 ml of anhydrous ether, there was added, dropwise, 28 g (0.197 mole) of methyl iodide in 50 ml of anhydrous ether. 26 g (0.160 mole) of tricyclo[6.2.1.0²,⁷]undec-9-en-3-one in 150 ml of ether were then added to and the above mixture, under vigorous stirring, the resulting reaction mixture was further refluxed for 24 hours. After cooling, the mixture was then decomposed by the addition of 200 ml of 20% aqueous solution of NH₄Cl at 0°. The organic layer was then extracted with ether (3×50 ml), washed with water (3×50 ml), dried over Na₂SO₄ and finally evaporated to yield 27 g of crude material.

The resulting obtained crude material was purified as follows: 27 g of said material were added to a mixture of 27 g of Girard P reagent, 27 ml of acetic acid and 270 ml of ethyl alcohol and then heated to reflux for 24 hours. After evaporation, the dry residue was diluted with 50 ml of water, extracted with ether (4×50 ml), and successively washed with water (3×50 ml), NaHCO₃ 10% in water (3×50 ml) and finally water. After drying over Na₂SO₄, filtration, evaporation and distillation, 14.7 g (51% yield) of the desired compound were isolated and had b.p. 55°–60°/0.3 Torr.

IR: 3448, 2857, 1449, 1366, 1134, 1022, 816 cm⁻¹.

NMR: 1.2 (3H, s); 1.3–2.0 (8H, m); 2.0–3.0 (5H, m); 6.2 (2H, m) δ ppm.

MS: m/e=97 (13), 95 (90), 94 (17), 79 (18), 67 (16), 66 (100), 43 (20).

EXAMPLE 2

3-Methyl-tricyclo[6.2.1.0²,⁷]undec-9-en-3-yl formate 13 g (0.127 mole) of acetic anhydride were first added under vigorous stirring and at 0° to 6 g (0.128 mole) of 98% aqueous formic acid, and the resulting mixture was then kept overnight at −5°.

7.4 g (0.042 mole) of 3-methyl-tricyclo[6.2.1.0²,⁷]undec-9-en-3-ol—see Example 1—were then added to the above mixture, and the whole mixture was stirred for 3 days at room temperature. The obtained mixture was then decomposed by the addition of 100 ml of a saturated aqueous solution of Na₂CO₃, extracted with ether (3×50 ml), washed with water (3×50 ml) and dried over Na₂SO₄. After evaporation 8 g of crude material were obtained which, by distillation at 0.02 Torr, provided the desired compound in a 58% yield.

IR: 2910, 1714, 1440, 1236, 1170, 1115, 1020, 910, 895, 782 cm$^{-1}$.

NMR: 1.0–3.1 (12H, several m); 1.6 (3H, s); 6.12 (2H, m); 8.05 (1H, d) δ ppm.

MS: m/e=160 (11), 134 (9), 117 (8), 95 (100), 94 (71), 79 (53), 66 (86), 53 (7), 39 (13).

EXAMPLE 3

3-Methyl-tricyclo[6.2.1.0$^{2,7}$]undec-9-en-3-yl acetate 10 g (0.056 mole) of 3-methyl-tricyclo[6.2.1.0$^{2,7}$]undec-9-en-3-ol—see Example 1—were added to 77 g (0.636 mole) of N,N-dimethyl-anilin, 77 g (0.980 mole) of acetyl chloride and 400 ml of CHCl$_3$ and the obtained mixture was heated to reflux for 4 hours. After cooling to room temperature, the reaction mixture was poured onto crushed ice (300 ml) and the organic layer extracted with CH$_2$Cl$_2$ (3×100 ml). After washing with 10% aqueous HCl, neutralization with aqueous 10% NaHCO$_3$ and finally with water (3×50 ml), drying over Na$_2$SO$_4$ and evaporation, 11.7 g of crude material were obtained. 6.8 g (55% yield) of the desired compound having b.p. 55°–60°/0.02 Torr were finally obtained by fractional distillation.

IR: 2915, 1724, 1570, 1449, 1362, 1239, 1117, 1022, 939, 897, 782 cm$^{-1}$.

NMR: 1.0–1.5 (5H, m); 1.5 (4H, s); 2.0 (4H, m); 2.1–3.0 (5H, m); 6.1 (2H, m) δ ppm.

MS: m/e=160 (17), 95 (100), 94 (88), 91 (17), 79 (64), 66 (82), 43 (46).

EXAMPLE 4

3-Methyl-tricyclo[6.2.1.0$^{2,7}$]undec-9-en-3-yl propionate 5 g (0.028 mole) of 3-methyl-tricyclo[6.2.1.0$^{2,7}$]undec-9-en-3-ol—see Example 1—and 47 g (0.50 mole) of propionyl chloride were reacted as indicated in Example 3 to provide, after extraction and evaporation, 6.5 g of crude material.

By distillation of the above material (b.p. 70°–75°/0.1 Torr), followed by purification by means of a column chromatography on silica gel (eluent cyclohexane/ether 7:3), 2.24 g (34% yield) of the desired compound were isolated. b.p. 65°–68°/0.1 Torr; m.p. ca. 30°

IR: 2882, 1712, 1449, 1333, 1181, 1114 cm$^{-1}$.

NMR: 1.08 (3H, t, J=7 Hz); 1,53 (3H, s); 1.1–1.6 and 1.8–3.0 (14H); 6.03 (2H, m) δ ppm.

MS: m/e=125 (17), 95 (34), 81 (16), 73 (21), 55 (31), 43 (100).

EXAMPLE 5

3-Methyl-tricyclo[6.2.1.0$^{2,7}$]undec-9-en-3-yl acrylate 5 g (0.028 mole) of 3-methyl-tricyclo[6.2.1.0$^{2,7}$]undec-9-en-3-ol—see Example 1—and 46 g (0.50 mole) of acrylyl chloride were reacted as indicated in Example 3 to provide 7 g of crude material.

By distillation (b.p. 65°–67°/0.1 Torr) and purification by means of column chromatography on silica gel (eluent cyclohexane/ether 7:3), 1.9 g (29% yield) of the desired compound were isolated. b.p. 68°–70°/0.1 Torr; m.p. 41°–42°

IR: 2899, 1704, 1613, 1443, 1395, 1198 cm$^{-1}$.

NMR: 1.1–3.1 (12H); 1.61 (3H, s); 5.56–6.53 (5H) δ ppm.

MS: m/e=160 (12), 95 (100), 94 (72), 79 (49), 66 (72), 55 (42).

EXAMPLE 6

3-Methyl-tricyclo[6.2.1.0$^{2,7}$]undec-9-en-3-yl isobutyrate 10 g (0.056 mole) of 3-methyl-tricyclo[6.2.1.0$^{2,7}$]undec-9-en-3-ol—see Example 1—and 7.5 g (0.070 mole) of isobutyryl chloride were reacted as indicated in Example 3 to provide, after extraction and distillation, 8 g of a material having b.p. 60°–85°/0.2 Torr.

By purification by means of column chromatography on silica gel (eluent cyclohexane/ethyl acetate 7:3), 6 g (43% yield) of the desired compound were isolated.

IR: 2899, 1724, 1460, 1339, 1248, 1136, 1062, 913 cm$^{-1}$.

NMR: 1.0–1.2 (6H, 2s); 1.3–1.5 (6H, m); 1.6 (3H, s); 1.9–3.0 (7H, broad m); 6.1 (2H, m) δ ppm.

MS: m/e=160 (11), 95 (100), 94 (48), 79 (26), 66 (59), 43 (42).

EXAMPLE 7

3-Methyl-tricyclo[6.2.1.0$^{2,7}$]undecan-3-ol 25 g (0.140 mole) of 3-methyl-tricyclo[6.2.1.0$^{2,7}$]undec-9-en-3-ol—see Example 1—in 150 ml of methanol were hydrogenated under atmospheric pressure and at room temperature in the presence of 2.5 g of 10% palladium on charcoal. After filtration, evaporation and distillation (b.p. 60°–65°/0.1 Torr), 24 g of a material containing ca. 90% of the desired compound according to vapor phase chromatographic analysis were isolated.

For its characterization, the above compound was further purified by means of a distillation on a spinning band column.

IR: 3484, 2857, 1449, 1357, 1121, 926 cm$^{-1}$.

NMR: 1.06 (1H, broad s); 1.22 (3H, s); 1.2–2.5 (16H) δ ppm.

MS: M$^+$=180 (23); m/e=162 (63), 134 (72), 95 (97), 79 (60), 71 (100), 43 (98).

EXAMPLE 8

3-Methyl-tricyclo[6.2.1.0$^{2,7}$]undec-3-yl formate 8.7 g of 3-methyl-tricyclo[6.2.1.0$^{2,7}$]undec-9-en-3-yl formate—crude material; see Example 2—in 60 ml of methanol were hydrogenated under atmospheric pressure and at room temperature in the presence of 0.8 g of 10% palladium on charcoal. After filtration and evaporation, the crude residue was extracted with ether (100 ml), washed with aqueous 10% NaHCO$_3$ (20 ml) and then with water to provide, after drying and evaporation, 8 g of crude material.

7 g of the above material were purified by means of column chromatography on silica gel (eluent cyclohexane/ether 7:3) to afford 2.2 g (25% yield) of the desired compound having b.p. 58°–60°/0.05 Torr.

IR: 2857, 1704, 1449, 1370, 1183, 1111 cm$^{-1}$.

NMR: 1.1–2.7 (16H); 1.57 (3H, s); 8.1 (1H, broad s) δ ppm.

MS: m/e=162 (54), 134 (96), 119 (42), 95 (100), 79 (75), 67 (50), 41 (47).

EXAMPLE 9

3-Methyl-tricyclo[6.2.1.0$^{2,7}$]undec-3-yl acetate 22 g (0.122 mole) of 3-methyl-tricyclo[6.2.1.0$^{2,7}$]undecan-3-ol—see Example 7—and 220 ml of isopropenyl acetate were refluxed for 6 hours, in the presence of 0.1 g of p-toluenesulfonic acid. After cooling to room temperature, the reaction mixture was washed with aqueous 10% NaHCO$_3$ (30 ml), then with water (3×30 ml), dried over $Na_2SO_4$ and evaporated to provide 24 g of crude material.

After distillation (b.p. 55°–70°/0.05 Torr) of the above material in the presence of $K_2CO_3$, 13 g (48% yield) of the desired compound were isolated.
IR: 2899, 1715, 1443, 1361, 1239, 1015 cm$^{-1}$.
NMR: 1.1–2.8 (16H); 1.52 (3H, s); 1.98 (3H, s) δ ppm.
MS: m/e=162 (52), 134 (100), 119 (47), 106 (61), 95 (90), 79 (70), 43 (74).

EXAMPLE 10

The following three compounds were used as perfuming ingredients for the manufacture of toilet soaps as indicated hereinafter (parts by weight):
Compound A: 3-methyl-tricyclo[6.2.1.0$^{2,7}$]undec-9-en-3-yl acetate
Compound B: 3-methyl-tricyclo[6.2.1.0$^{2,7}$]undec-3-yl acetate
Compound C: 3-methyl-tricyclo[6.2.1.0$^{2,7}$]undec-9-en-3-yl formate

| Ingredients | Sample A | Sample B | Sample C |
|---|---|---|---|
| Commercial soap paste | 100 | 100 | 100 |
| Compound A | 1 | — | — |
| Compound B | — | 1 | — |
| Compound C | — | — | 1 |

The thus perfumed paste was then manufactured according to the usual techniques and the obtained perfumed samples were finally subjected to an olfactive evaluation which gave the following results:
Sample A: fresh, green and natural lifting odor; reminiscent of certain aspects of clary sage oil
Sample B: woody odor with amber-like and green notes; reminiscent of clary sage oil
Sample C: woody and amber-like odor with green and aromatic notes; reminiscent of sweet marjoram oil.

EXAMPLE 11

A perfumed detergent powder was prepared by intimately mixing the following ingredients (parts by weight):

| Ingredients | Sample A | Sample B | Sample C |
|---|---|---|---|
| Commercial detergent powder[1] | 100 | 100 | 100 |
| Compound A[2] | 0.15 | — | — |
| Compound B[2] | — | 0.15 | — |
| Compound C[2] | — | — | 0.15 |

[1]contains enzymes and perborates
[2]see Example 10

The thus perfumed samples were then subjected to an olfactive evaluation which gave the following results:
Sample A: pleasant green and fresh odor; reminiscent of clary sage
Sample B: slightly woody odor of green type with amber-like and aromatic notes
Sample C: woody and amber-like odor with green and aromatic notes; reminiscent of sweet marjoram.

It was further observed in the above three cases that the imparted odor remained unchanged after several week storage under the usual conditions. Moreover, it was apparent that towels treated with the perfumed detergent powder possessed a fragrance which remained on the material after washing.

EXAMPLE 12

A perfumed shampoo was prepared by mixing the following ingredients (parts by weight):

| Ingredients | Sample A | Sample B | Sample C |
|---|---|---|---|
| Commercial shampoo base | 100 | 100 | 100 |
| Compound A[1] | 0.20 | — | — |
| Compound B[1] | — | 0.20 | — |
| Compound C[1] | — | — | 0.20 |

[1]see Example 10

The thus perfumed shampoos were then subjected to an olfactive evaluation which gave the following results:
Sample A: fresh and green lifting odor of "herbal shampoo" type
Sample B: slightly woody, green and amber-like odor; analogous to sample A
Sample C: woody, amber-like odor with green and aromatic notes; "medicinal"-like.

EXAMPLE 13

A perfume base for classical Eau de Cologne was prepared by mixing the following ingredients (parts by weight):

| | |
|---|---|
| Lemon oil | 250 |
| Bergamot oil | 300 |
| Orange oil | 150 |
| Petitgrain bigarade | 100 |
| Neroli bigarade | 20 |
| Lavender oil | 70 |
| Thyme oil | 10 |

After dilution of the above base at 3% in 95% ethyl alcohol there is obtained a classical Eau de Cologne with a warm and citrus-like odor.

By adding to 95 parts of the above Eau de Cologne 5 parts of a 10% solution of 3-methyl-tricyclo[6.2.1.0$^{2,7}$]undec-9-en-3-yl acetate in 95% ethyl alcohol, there was obtained a novel Eau de Cologne possessing a more lifting odor together with a pleasant "masculine" character.

An analogous effect was observed when, in the above example, 3-methyl-tricyclo[6.2.1.0$^{2,7}$]undec-9-en-3-yl acetate was replaced by 3-methyl-tricyclo[6.2.1.0$^{2,7}$]undec-3-yl acetate or 3-methyl-tricyclo[6.2.1.0$^{2,7}$]undec-9-en-3-yl formate.

EXAMPLE 14

A perfume base for masculine Eau de toilette was prepared by mixing the following ingredients (parts by weight):

| | |
|---|---|
| Linalyl acetate | 100 |
| Oak moss absolute 50%* | 80 |
| p-t-Butyl-cyclohexyl acetate | 70 |
| Lemon oil | 70 |
| Cedryl acetate | 60 |
| Orange oil of Florida | 50 |
| Lavender oil | 50 |
| Synthetic bergamot oil | 50 |
| Isobornyl acetate | 40 |
| EXALTEX®[1] | 40 |
| Ambrette musc | 30 |
| Oriental sandal wood oil | 60 |
| Eugenol | 20 |
| Thyme oil 10%* | 20 |
| β-Damascenone 1%* | 20 |

| | |
|---|---|
| Neroli oil of Portugal | 10 |
| Coumarin | 10 |
| Lavender absolute | 10 |
| AMBROX ®[1] 1%* | 10 |
| Total | 800 |

*in diethyl phthalate
[1] origin: FIRMENICH SA, Geneva/Switzerland

The thus prepared base composition possesses an odor of "chypre" type.

By adding to 80 parts of the above base 20 parts of 3-methyl-tricyclo[6.2.1.0$^{2,7}$]undec-9-en-3-yl acetate a novel perfume composition developing a fuller, rounder and more harmonious odor than that of the base was obtained.

An analogous effect was observed when, in the above example, 3-methyl-tricyclo[6.2.1.0$^{2,7}$]undec-9-en-3-yl acetate was replaced by 3-methyl-tricyclo[6.2.1.0$^{2,7}$]undec-3-yl acetate or 3-methyl-tricyclo[6.2.1.0$^{2,7}$]undec-9-en-3-yl formate. In this latter case moreover, the obtained perfume composition developed a pleasant woody and amber-like note.

What we claim is:

1. A method for modifying, improving or enhancing the organoleptic properties of perfumes or perfumed articles which comprises adding thereto an olfactive effective amount of a compound having the formula:

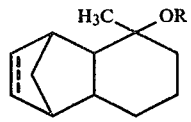

wherein the dotted line represents a single or a double bond and the symbol R represents either a hydrogen atom or a saturated or unsaturated acyl radical containing from 1 to 6 carbon atoms.

2. A perfume composition containing an olfactive effective amount of a compound having the formula:

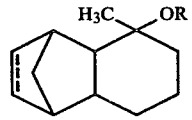

wherein the dotted line represents a single or a double bond and the symbol R represents either a hydrogen atom or a saturated or unsaturated acyl radical containing from 1 to 6 carbon atoms.

* * * * *